United States Patent [19]

Enzer et al.

[11] 4,336,121

[45] Jun. 22, 1982

[54] APPARATUS FOR MEASURING ELECTROCHEMICAL ACTIVITY

[75] Inventors: Steven E. Enzer, Brooklyn; Robert J. Sarrine; William L. Wilfong, both of Ann Arbor, all of Mich.

[73] Assignee: Transidyne General Corporation, Ann Arbor, Mich.

[21] Appl. No.: 216,461

[22] Filed: Dec. 15, 1980

[51] Int. Cl.³ ............................................ G01N 27/28
[52] U.S. Cl. .............................. 204/195 R; 23/230 B; 23/928; 204/195 B; 324/425; 324/438; 422/68
[58] Field of Search ............... 204/195 R, 195 B, 1 H, 204/274; 422/68; 23/928, 230 B; 324/425, 438

[56] References Cited

U.S. PATENT DOCUMENTS

| | | | |
|---|---|---|---|
| 3,049,118 | 8/1962 | Arthur et al. | 204/195 G X |
| 3,399,667 | 9/1968 | Nishimoto et al. | 204/195 G X |
| 3,892,652 | 7/1975 | Levine et al. | 204/195 R |
| 3,911,901 | 10/1975 | Niedrach et al. | 204/195 R X |
| 4,115,230 | 9/1978 | Beckman | 204/195 R |
| 4,119,498 | 10/1978 | Edwall et al. | 204/1 T |
| 4,272,245 | 6/1981 | Diamond et al. | 23/230 B |

*Primary Examiner*—G. L. Kaplan
*Attorney, Agent, or Firm*—Krass, Young & Schivley

[57] ABSTRACT

Apparatus is disclosed for measuring the electrochemical activity of a liquid, for example, the hydrogen ion activity or pH value of blood. A disposable cartridge includes spaced indicating and reference electrodes which develop electrical properties as a function of the electrochemical activity. The cartridge carries a capsule containing an electrolyte solution. A machine for measuring the electrochemical activity includes a socket in a pivoting door for receiving the cartridge. When the door is pivoted into a closed position, the capsule is automatically crushed thereby covering the electrodes with the solution. The breaking of the capsule triggers an electronic measurement of the resultant electrical properties that develop between the two electrodes. This calibration factor is stored and used to compute the electrochemical characteristics of the sample when it is introduced into the cartridge to cover the indicating electrode. In one embodiment a photocell arrangement emits light which is absorbed by the sample so as to automatically trigger the final measurement when the sample is in contact with the indicating electrode. The cartridge is heated to a predetermined temperature to insure the accuracy of the measurement. Preferably, the socket assembly includes heater pads on opposing printed circuit boards which come into contact with the cartridge when the door is closed. The cartridge has a thermally conductive insert adjacent the tip of the indicating electrode which is contacted by a sensor in the socket to provide signals to a microcomputer which is adapted to control the measurement process.

6 Claims, 13 Drawing Figures

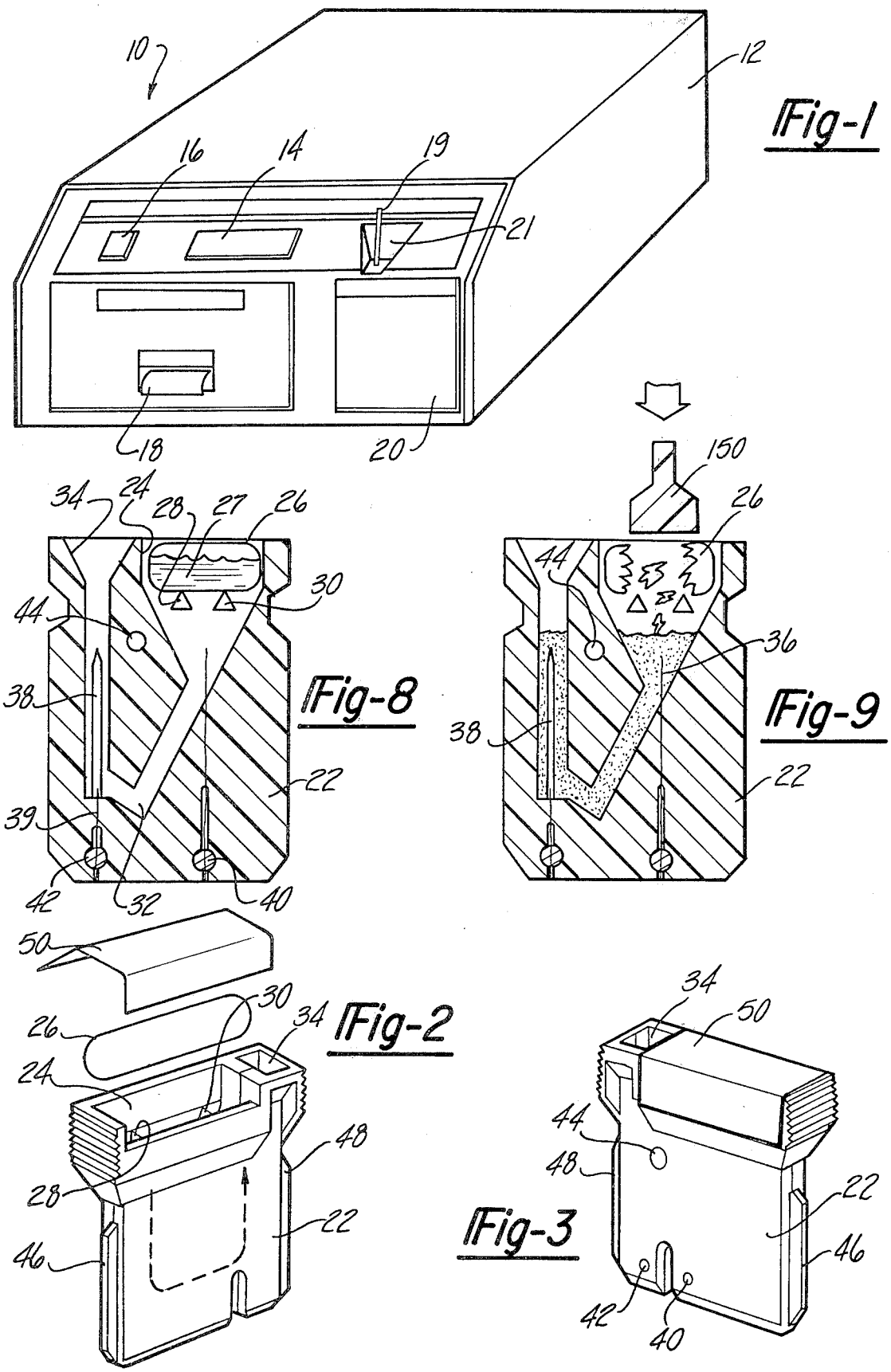

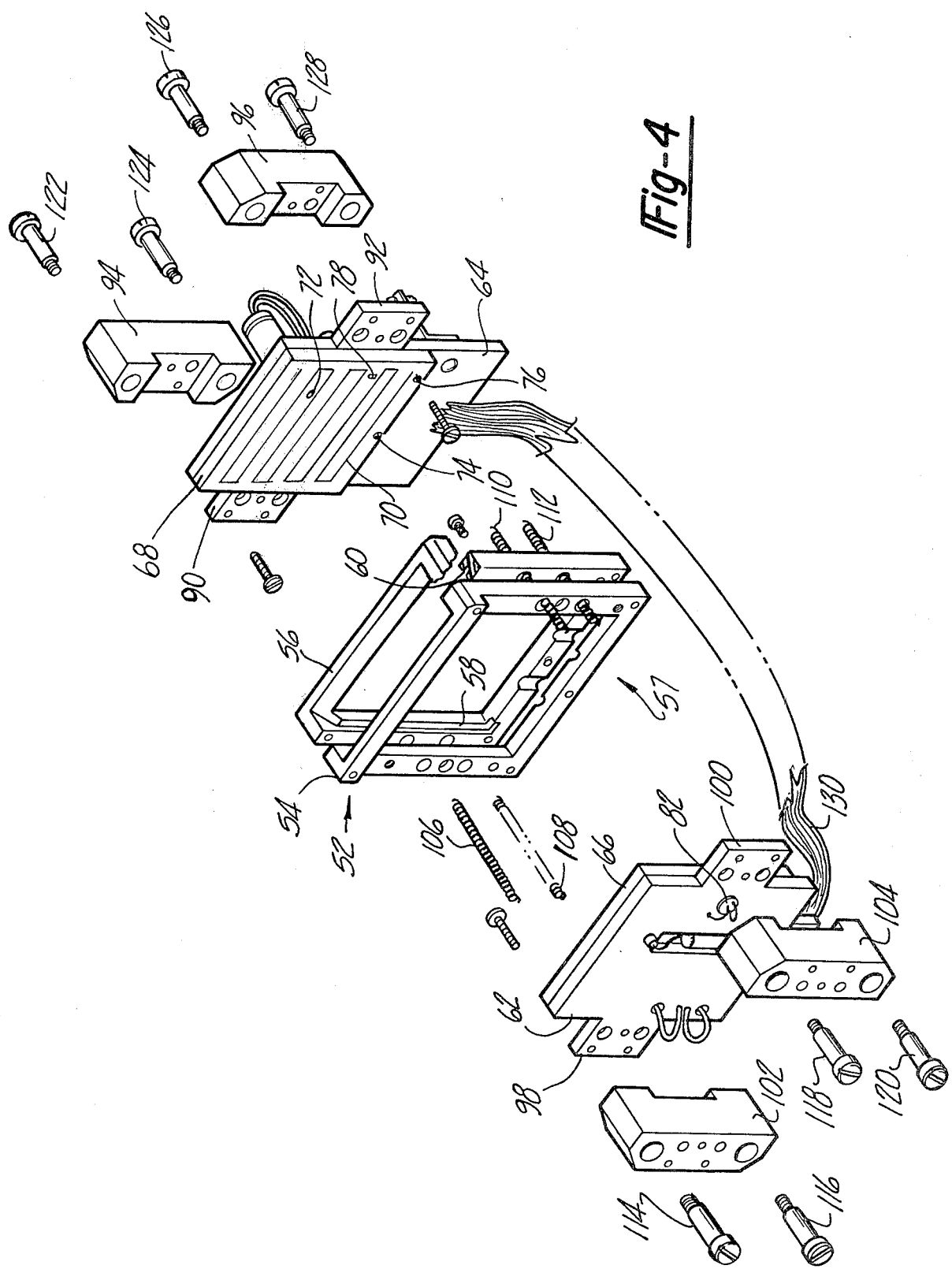

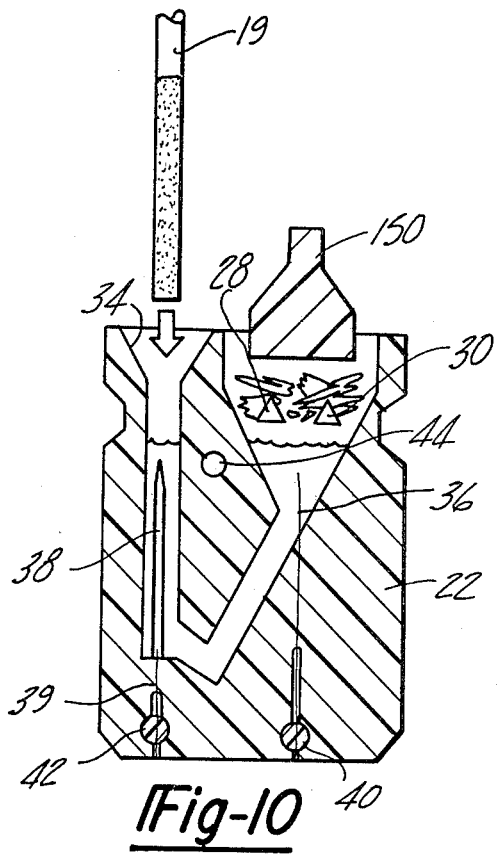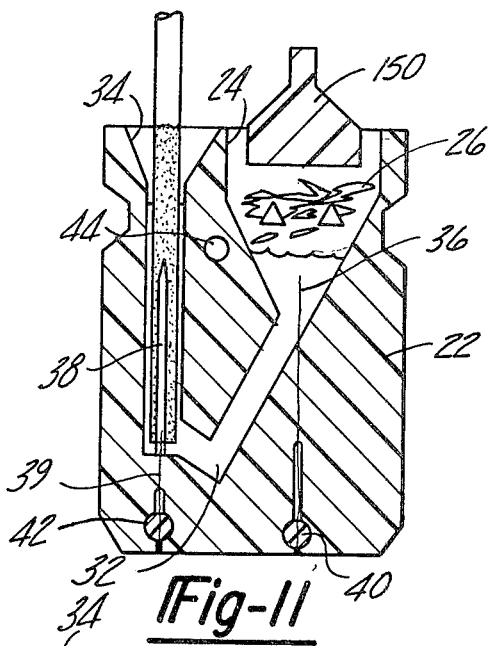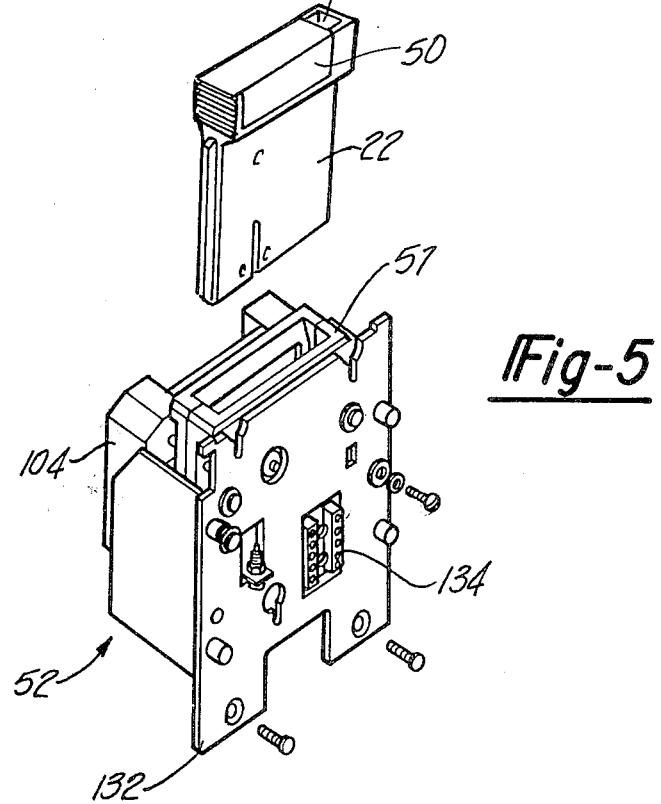

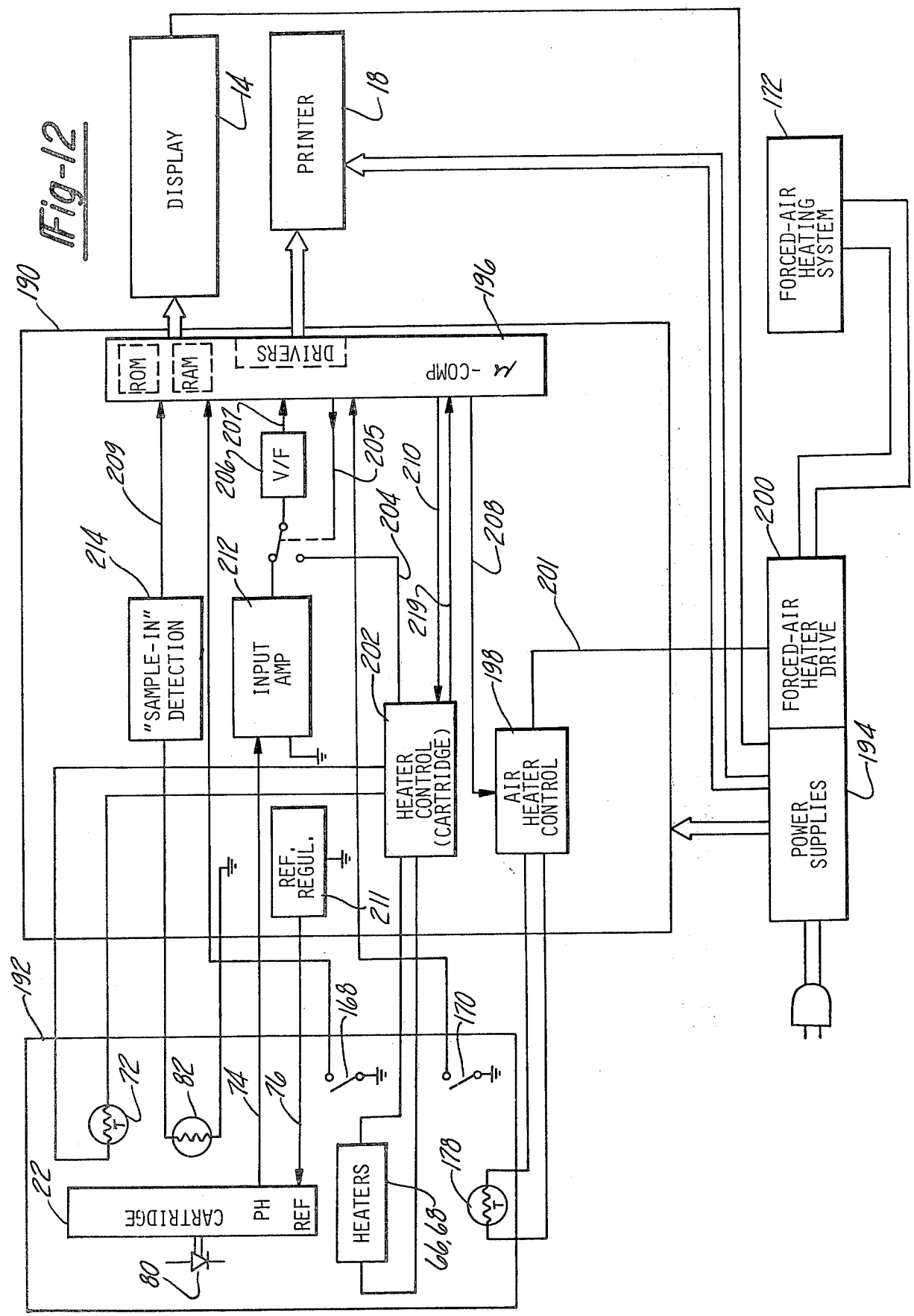

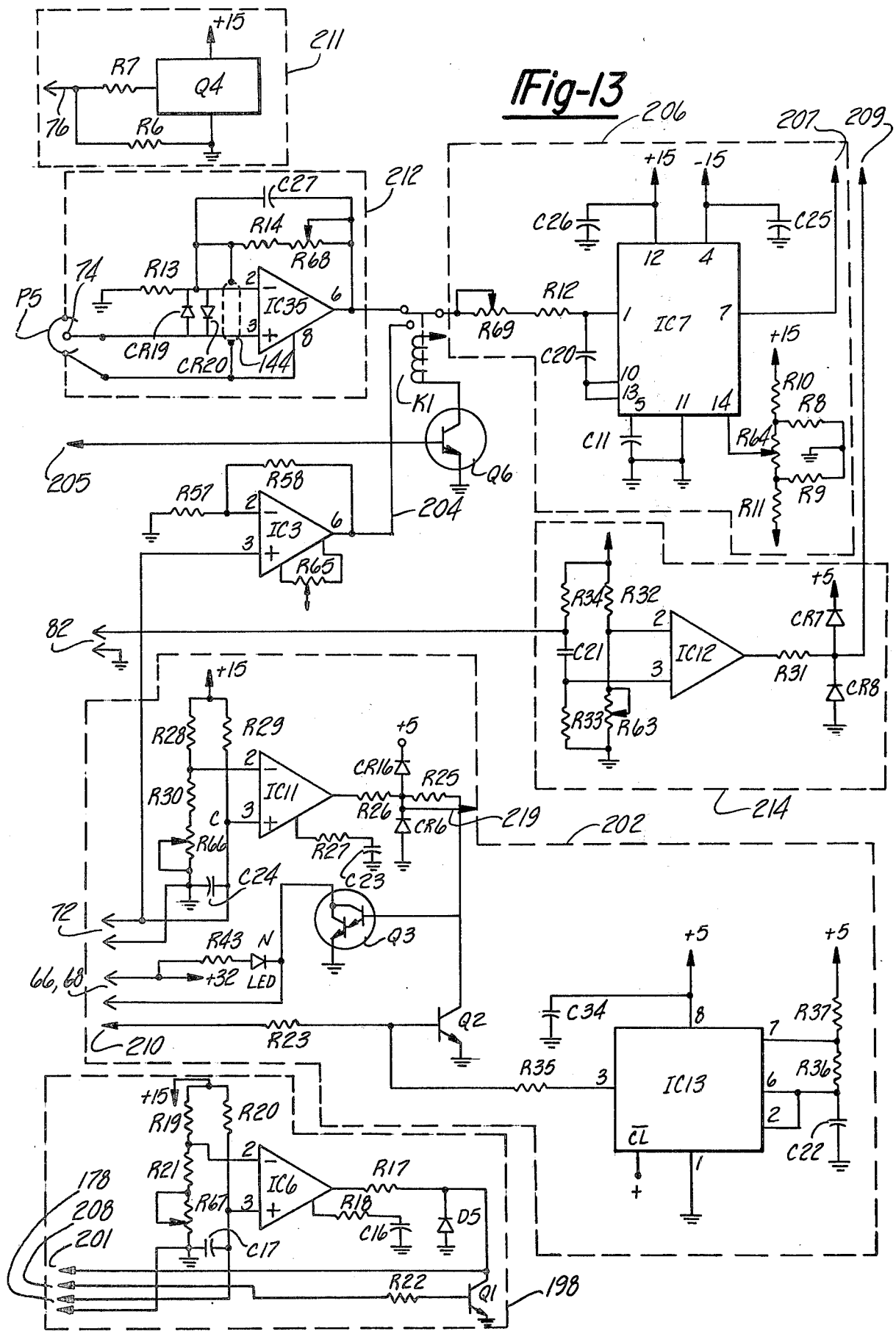

APPARATUS FOR MEASURING ELECTROCHEMICAL ACTIVITY

BACKGROUND OF THE INVENTION

This invention relates to apparatus for measuring electrochemical characteristics of a liquid, for example, the pH value of a blood sample.

The pH value of blood is a frequently measured physiological parameter which provides an indication of proper acid-base balance and blood-gas exchange through the lungs. In the field of obstetrics, pH tests are often made if there are indications of fetal distress during labor which may be caused by the fetus not receiving sufficient oxygen from the mother due to strangulation by the umbilical cord or premature separation of the placenta. Conventionally, the blood samples are taken by making a small incision on the fetal scalp and placing a capillary tube in the proximity of the incision whereby the blood is drawn up into the interior portions of the tube through capillary action.

One of the most commonly used clinical devices for measuring the blood pH is the blood-gas analyzer such as the pH blood-gas system manufactured by Corning Medical Corporation or the PHM71 Mk2 acid-base analyzer from Radiometer-Copenhagen. The pH sensor is of traditional construction using pH sensitive glass such as Corning Glass Works Type 01500 which has been formed into a cylindrical envelope in which is sealed an internal electrolyte and reference electrode. The sensing surface of the electrode is placed in contact with the blood, which in turn is contacting a reference electrode via an electrolyte junction. The system is maintained at a preselected temperature by way of a relatively complex circulating heated water bath.

These typical pH analyzers are calibrated at two pH values, generally 6.83 and 7.38, which allows adjustment for both electrode sensitivity and absolute potential. This two point calibration is somewhat complex necessitating relatively sophisticated electronics normally used by trained personnel.

Such analyzers generally require the transfer of the blood sample from the capillary tube to a receptacle in the instrument. As is known in the art, if any ambient air mixes with the blood sample, the pH value will change. Hence, there is a possibility of contaminating the blood sample during the transfer from the original collecting device to the instrument.

Since such analyzers are complex and costly devices, they are typically located only in the hospital laboratory where they are operated by skilled technicians. As a result, there is often considerable delay between the time of taking the blood sample until the results from the lab are received. Of course, such delays are undesirable in emergency situations.

U.S. Pat. Nos. 3,911,901 to Neidrach et al, 3,049,118 to Arthur et al, 3,399,667 to Nishimoto et al, 4,119,498 to Edwall et al and 3,892,652 to Levine et al disclose representative devices for measuring electrochemical activities of various samples. However, each of them, like the analyzers noted above, have drawbacks and do not readily lend themselves to fast, convenient and accurate pH measurements by relatively untrained personnel.

Many of these problems, however, are solved by the method and apparatus disclosed in commonly assigned U.S. patent application Ser. No. 965,901, now U.S. Pat. No. 4,272,245, to Diamond et al which discloses the broad concept of utilizing a disposable cartridge containing indicating and reference electrodes. A common electrolytic solution is used to establish a one point calibration factor and also serves as an electrolytic bridge during measurement of the sample. The sample is collected in a capillary tube and the cartridge is adapted to receive the blood sample directly from the tube. The capillary tube is slipped over the indicating electrode so that the blood displaces the solution and covers the indicating electrode. The electrical properties between the two electrodes are again measured and used to calculate the electrochemical activity (e.g. pH) of the sample in conjunction with the previously measured calibration factor. This application is hereby incorporated by reference.

The present invention is directed to improvements to this general concept. More particularly, an entire system is designed pursuant to various features of this invention that permits fast, convenient, and accurate measurements of electrochemical activity of liquid samples without requiring the need for trained personnel to operate the equipment.

SUMMARY OF THE INVENTION

According to one aspect of this invention, provision is made for quickly bringing and accurately maintaining the liquid sample at a predetermined temperature during the measurement process. Thermally conductive means on the cartridge housing is adapted for receipt of a sensor for sensing the temperature of the liquid. The cartridge is designed to be slidably mounted in a socket attached to a pivoting door of an electronic measurement machine. The socket includes two opposing plates which come into contact with the cartridge. The temperature sensor is adapted to engage the thermally conductive means on the housing and provides an output signal to control the heating of the cartridge. Preferably, the plates include heater pads which are energized for a time period which is a function of the initial temperature of the cartridge thereby serving to quickly bring the components in the cartridge to the desired temperature.

Advantageously, the opposing plates are resiliently coupled together and operate to clamp the cartridge between them when the door is pivoted to a closed position. The cartridge preferably employs an ampule containing an electrolyte solution which rests in a trough in the cartridge. Means are provided for breaking the capsule when the door is pivoted to the closed position. A sensing arrangement is provided for detecting the condition of the ampule and serves to trigger a calibration measurement when the capsule is broken to cover the electrodes with the solution. The data is stored in a memory and is later retrieved for use in calculating the final value. The final measurement is triggered when the liquid sample is introduced to cover the indicating electrode. Pursuant to a feature of this invention the introduction of a blood sample is detected by a photocell arrangement mounted on the opposing plates of the socket. Preferably, a light source is used which emits light having a wavelength which is absorbed by the liquid whereby the introduction of the sample is detected. A forced air heater system may be utilized to cooperate with the heater pads in the socket to keep the cartridge at the critical temperature. Both heaters are selectively disabled during measurements to prevent electrical noise from disturbing the accuracy thereof.

BRIEF DESCRIPTION OF THE DRAWINGS

These and other objects and advantages of the present invention will become apparent upon a reading of the following specification and by reference to the drawings in which:

FIG. 1 is a perspective view of the preferred embodiment of the machine of the present invention;

FIG. 2 is an exploded perspective view of the cartridge of the present invention;

FIG. 3 is a perspective view of the cartridge with the ampule mounted therein;

FIG. 4 is an exploded perspective view of the socket assembly used in the machine of the preferred embodiment;

FIG. 5 is a perspective view of the completed socket assembly;

FIGS. 8-11 schematically illustrate the operational sequence of the measurement process utilizing the apparatus of the present invention;

FIG. 12 is a block diagram of the electrical circuitry used in the preferred embodiment; and FIG. 13 is a detailed schematic of the circuitry.

DESCRIPTION OF THE PREFERRED EMBODIMENT

Figure 7:
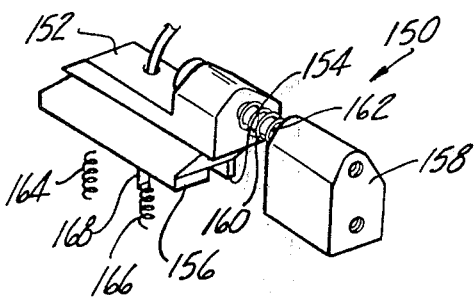
FIG. 7 is a perspective view of the ampule crushing mechanism employed in the preferred embodiment.

It should be noted that from the outset that while the present invention finds particular utility in measuring the pH value of a blood sample, it may also be used to measure a wide variety of electrochemical activities, for example, the concentration of oxygen, sodium, potassium, and carbon dioxide in liquid samples depending on the ion reactive nature of the electrode materials used. Still other uses of this invention will become readily apparent to one skilled in the art.

Turning now to FIG. 1, an electronic measurement machine 10 includes a generally rectangular housing 12 for the internal measuring electronics and related components. The front panel of housing 10 includes a display 14, an on/off button 16 and a printer 18. A door 20 is pivotably mounted on housing 12. The door 20 is hinged about its lower edge such that the door tilts outwardly for receipt of cartridge 22. After receiving cartridge 22 the door is pivoted to its closed position shown in FIG. 1 where a capillary tube 19 containing the blood sample may be inserted into the cartridge 22 through an indention 21 in the front panel above an opening in the top of the cartridge as will later be described in detail.

Cartridge 22 is shown most clearly in FIGS. 2, 3 and 8-11. It is made of clear polystyrene plastic and includes an open ended trough 24 for supporting a glass ampule 26 containing an electrolyte solution 27. With special references to FIGS. 8-11, the lower portions of trough 24 are defined by pointed cross bar members 28 and 30. Trough 24 empties into a generally U-shaped channel 32 which terminates in an opening or throat 34 in the upper end of cartridge 22 next to trough 24.

Lower portions of a reference electrode 36 are sandwiched lengthwise within the solid portion of the cartridge housing. However, the sensitive tip of reference electrode 36 projects into one leg of channel 32 as shown. Reference electrode 36 is made of a silver chloride wire but may be constructed of various materials depending upon the application. Indicating electrode 38 is mounted in the other leg of channel 32. Indicating electrode 38 again may be made of a variety of appropriate materials but in this embodiment consists of transparent pH sensitive glass. Transversely mounted electrically conductive plugs 40 and 42 of conductive epoxy serve to make electrical contact with the lower ends of electrode 36 and a conductive wire 39 connected to electrode 38, respectively.

Cartridge 22 includes an insert 44 of a thermally conductive material which is embedded in one surface of the cartridge housing adjacent the tip of indicating electrode 38. Preferably, insert 44 consists of silicone rubber. As will be described later herein, insert 44 cooperates with a temperature sensing probe for sensing the temperature of the cartridge 22 when it is initially inserted into machine 10.

Two laterally extending ridges 46 and 48 are provided on the sides of cartridge 22. Each ridge is of a different cross sectional dimension and serves to assist in correctly orienting the cartridge 22 into the socket assembly 52 mounted on the door 20.

A flexible tape 50 completes the cartridge 22 and operates to hold the ampule 26 in place. Note that tape 50 does not cover throat 34 which remains unobstructed for receipt of the capillary tube 19 containing the liquid sample.

Turning now to FIGS. 4-7, the socket assembly 52 will be described. As can be seen most clearly in FIG. 4, the socket 52 includes a frame 57 made up of two mating members 54 and 56 which cooperate to form an open ended receptacle for receiving cartridge 22. Vertically extending slots 58 and 60 on the outer edges of the frame 57 cooperate to define a keyed guideway for the cartridge ridges 46 and 48. The widths of slots 58 and 60 are of different sizes and conform to the thicknesses of ridges 46 and 48 such that cartridge 22 can be placed within the socket only in one orientation. This assures that the electrode contacts 40, 42 and thermal sensor insert 44 will be facing in the right direction to contact the sensors in the socket assembly.

A pair of circuit boards 62 and 64 are mounted on opposing sides of the frame 57. Circuit boards 62, 64 include heater pad plates 66 and 68, respectively, each having a serpentine pattern of electrically conductive filaments 70 etched in its outer face.

A temperature sensor probe 72 projects through the outer surface of plate 68 and is spaced from the heater filaments thereon. Sensor 72 is located such that it aligns with the thermally sensitive contact area 44 on cartridge 22 when it is inserted into the socket. Similarly, conductive pins 74 and 76 are arranged to come into contact with the electrically conductive plugs 40 and 42 on cartridge 22. A window 78 provides an opening for a light source such as a light emitting diode (LED) 80 as can be seen most clearly in FIG. 6. A photosensitive device such as a photoresistor 82 is mounted within an aligned opening 84 within circuit board 62 and heater plate 66. This photocell arrangement is arranged to be in alignment with the tip of the indicating electrode 38 when the cartridge 22 is inserted into the socket assembly 52. Preferably, the light source 80 is chosen such that it emits light having a wavelength absorbed by the liquid sample to be tested. Where the liquid sample is blood, LED 80 is such that it emits a green light which is absorbed by the blood for the purposes to be later explained. Note that the cartridge 22, indicating electrode 38, and the capillary tube 19 are all transparent.

With particular reference again to FIG. 4, the laterally extending flanges 90 and 92 of circuit board 64 are coupled to corresponding recesses in connectors 94 and 96, respectively. Likewise, flanges 98 and 100 of circuit board 62 are coupled to corresponding recesses in connectors 102 and 104, respectively. It is a feature of this invention that the two circuit board subassemblies are resiliently biased in opposed directions such that in an uncompressed condition the inner faces of heater plates 66 and 68 are spaced from the outerwalls of cartridge 22 when it is initially inserted into the socket assembly 52. This is accomplished in the preferred embodiment by way of springs 106–112 which pass through openings in frame 57. The opposite ends of these springs abut the connectors of the two opposing circuit board subassemblies. Pins 114–128 include threaded end portions which engage openings in the frame 57 to attach the circuit board subassemblies thereto. Note, however, that each subassembly is free to move an appreciable distance along the unthreaded shafts of the pins such that each circuit board, normally biased outwardly by the springs, may move toward one another when compressed.

Electrical connection between the two circuit boards is made by way of a ribbon cable 130. FIG. 5 shows the completed socket assembly 52 which includes a cover plate 132 connected to the outer surface of connector 94 and 96. A dual-in-line package connector block 134 provides electrically conductive paths between the components on the socket assembly 52 and the electronics contained within the machine 10.

Figure 6:
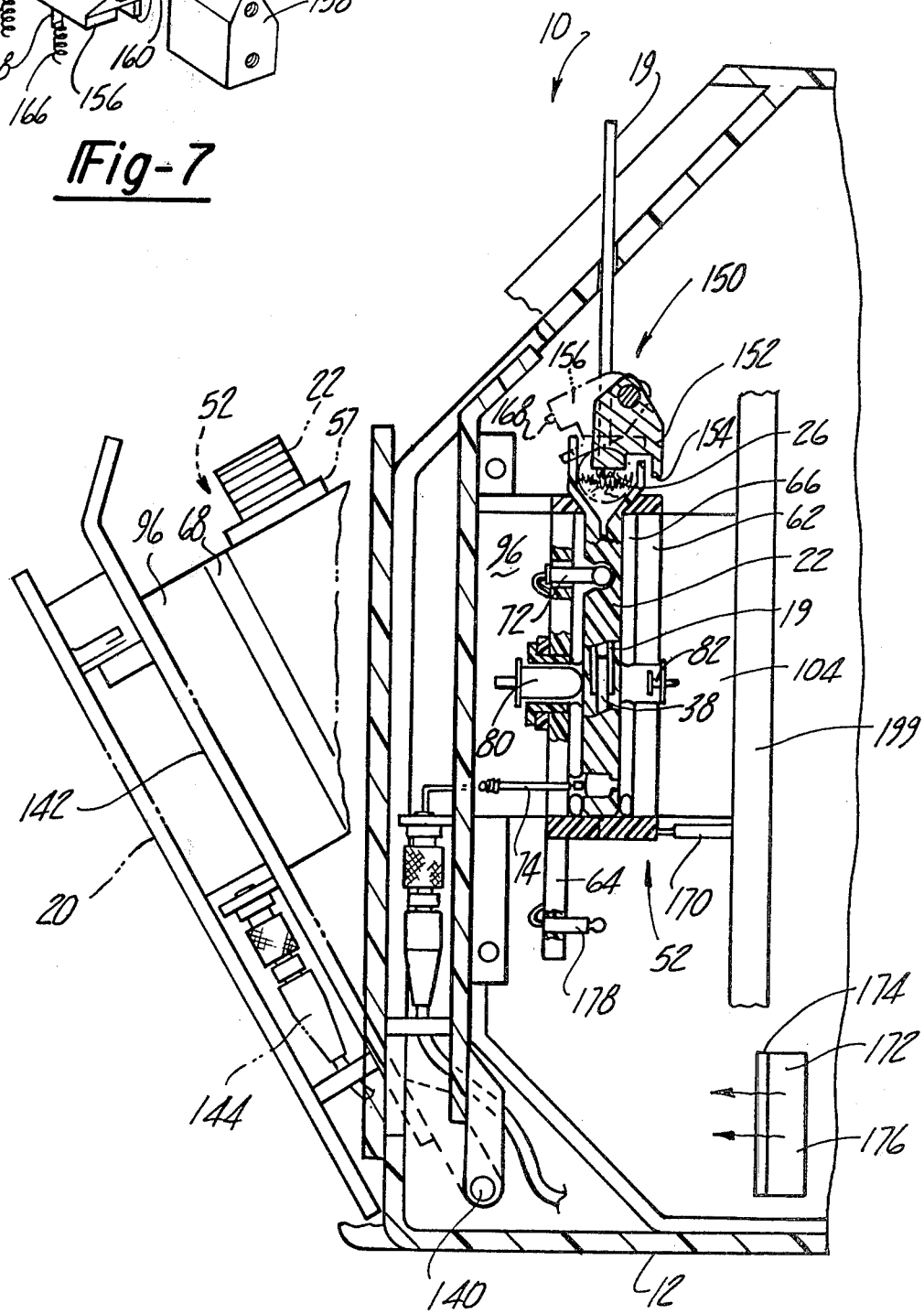
FIG. 6 is a cross sectional view of the door assembly shown in open and closed positions.

Turning especially to FIG. 6, door 10 is shown in both open and closed positions. In the open position door 20 pivots outwardly about axis 140 away from the vertical front surface of housing 12. Socket assembly 52 is mounted on the inner surface of door 20. In this embodiment socket assembly 52 is attached by way of conventional screws (not shown) to an inner wall 142 of door 20. Electrical connection to the components on socket assembly 52 is made by conventional means. For example, a coaxial cable 144 is shown for making electrical connection to pin 74 connected to indicating electrode 38. The exact method of making the various electrical connections is well within the skill of the ordinary practitioner. With door 20 in the open position, a new cartridge 22 may be placed into the socket assembly 52.

Special attention should now be drawn to the crusher mechanism 150 shown in FIGS. 6 and 7. A body 152 of rigid non-conductive material such as polycarbonate has a U-shaped end portion defining elongated lip 154 and leg 156 portions therein. Body 152 is pivotally connected to block 158 which is rigidly mounted on structural members in housing 12 of machine 10. Body 152 is resiliently biased against counter clockwise rotation by a coil spring 160 surrounding a connecting shaft 162, with the ends of the spring 160 being connected to body 152 and block 158. Crusher mechanism 150 is mounted within housing 12 above socket assembly 52 and in alignment with trough 24 of the cassette 22 when door 20 is closed as can be seen most clearly in FIG. 6. The phantom lines in FIG. 6 represent the orientation of body 152 caused by spring 160 when the door 20 is open. When door 20 is pivoted to the closed position, lip 154 of the crusher mechanism 150 is struck by the upper right hand corner of the cartridge 22 causing the body 152 to be rotated counter clockwise such that the leg 156 comes into engagement with the ampule 26. The downward force of leg 156 breaks ampule 26 causing it to disperse the electrolyte solution 27 into channel 32 to cover the electrodes.

Crusher mechanism 150 also includes two downwardly projecting springs 164, 166 which operate to push down on the tape 50 covering capsule 26. A contact switch 168 projects downwardly from leg 156 between springs 164, 166. Switch 168 operates to provide an electrical indication of the state of ampule 26. Assuming that ampule 26 is intact as it should be in the case for a new cartridge, the plunger element of switch 168 will first be pushed upwardly by ampule 26 and then allowed to traverse downwardly into the trough 24 portion formerly occupied by the volume of the ampule 26 after it is broken. This reciprocating motion of contact switch 168 is sensed by the internal machine electronics to indicate: (1) that a good cartridge 22 with a full ampule 26 was used in the first place and, (2) that the ampule 26 as subsequently broken to introduce the electrolyte solution into the channel 32 of cartridge 22. Springs 164, 166 serve to hold tape 50 down so as to not interfere with the sensing process. It should be appreciated that if the user attempted to use an old cartridge in which ampule 26 had already been broken, contact switch 168 would not encounter the necessary reciprocating motion, i.e., the upward motion signifying that a good ampule 26 is in place, followed by the downward motion indicating that the ampule 26 has been broken.

The machine housing 12 also includes a door switch 170 which serves to provide an electrical signal indicative of the position of door 20. This may be accomplished by way of a contact switch 170 which is hit by part of the socket assembly 52 when the door is closed. Various other constructions can be readily utilized.

Machine housing 12 incorporates a forced air heating system representing by the block 172 in FIG. 6. Forced air heating system 172 includes a heater grid 174 containing five twelve-watt resistors and a 60 CFM squirrel cage blower 176 for blowing air through the grid 174 towards socket assembly 52. The purpose of the forced air heating system is to cooperate with the heater pads 66, 68 of the socket assembly 52 to maintain the liquid sample to be tested at a very precise temperature. A thermistor 178 senses the temperature surrounding the socket assembly 52 and provides electrical signals for controlling the operation of the forced air heater system 172.

The cooperation of the heater pads and the forced air heating system serves to provide a unique method by which the cartridge is quickly and accurately maintained at the temperature at which the test measurements are taken to insure precise results. The low thermal mass of the heater pads permit them to be quickly raised in temperature and then quickly turned off to prevent substantial over-shooting of the desired temperature. It has been found that heating the cartridge by way of the heater pads above does not always maintain the cartridge at the desired temperature since thermal losses through the edges, particularly the open-ended top of the cartridge, may cause undesirable thermal gradients within the cartridge. This condition is aggravated when the temperature difference between the desired test temperature and the ambient is substantial. The forced air heating system provides a locally stable temperature environment which is insensitive to ambient conditions. This latter system maintains the cartridge at a completely uniform temperature after the heater pads produce the rapid temperature rise to initially bring the cartridge to the necessary temperature. This dual system heating approach is particularly advantageous when compared to other heating methods such as water baths, thermal blocks, and ovens which either do not allow for sufficient thermal conductivity to meet the time constraint on quick temperature rise or implementation in a mechanically and electrically efficient manner. It should, however, be understood that one skilled in the art will undoubtedly be capable of devising other heating systems which provide the above noted functions using the teachings of this application as a guide.

FIG. 12 is a block diagram of the electronic circuitry for machine 10. Block 190 represents the printed circuit board on which the electronics reside whereas block 192 represents that portion of the machine in which the cartridge sensing takes place. For ease in correlating the various elements with the other figures, common reference numerals will be utilized whenever possible.

A power supply 194 supplies power from an AC line source to the various components at the necessary voltage levels in a known manner. The system is based around an eight-bit microcomputer 196 such as the Intel 8080A microprocessor system which includes onboard RAM and ROM memory and output drivers as is well known in the art. Since microprocessor based systems are so well known in the art, the particulars of the connections between the various components making up microcomputer 196 will not be described in detail. Such information is readily available from the manufacturer and other publicly available sources. Microcomputer 196 will contain a program in either the random access memory or read only memory portions of the system which is adapted to perform the functions to be described herein. A skilled practitioner will be readily able to program microcomputer 196 to perform such functions in view of the description herein without undue experimentation.

Air sensor thermistor 178 is coupled to a heater control circuit 198 which controls the drivers 200 of the forced air heating system 172 as a function of the temperature sensed by thermistor 178.

Door switch 170 is coupled to microcomputer 196 to provide an indication of the door 20 position. Likewise, contact switch 168 provides signals to microcomputer 196 to indicate the status of cartridge ampule 26 as described above.

Cartridge sensing thermistor 72 is coupled to a cartridge heater control circuit 202. Circuit 202 provides an analog output signal on line 204 which is a function of the temperature sensed by thermistor 72. This analog signal is converted to a digital representation suitable for use with microcomputer 196 by a voltage to frequency converter 206. Voltage to frequency converters are well known in the art and operate to convert the voltage level of the analog input signal to digital signals having a frequency dependent upon the voltage level of the input signal. In the preferred embodiment, converter 206 is a VFC32 manufactured by Burr-Brown. Conveniently, converter 206 can be used to convert signals from a variety of sources into digital form over line 207 to microcomputer 196. In FIG. 12, relay K1 schematically represents a means for switching between inputs from various sources. Relay K1 is controlled by an output signal on line 205 from microcomputer 196 and may take various forms such as conventional relays or multiplexing arrangements. Output lines 208, 210 operate to disable the heater control circuits 198 and 202.

The reference electrode 36 in cartridge 22 is maintained at a preselected voltage level by way of regulator circuitry 211 connected to contact pin 76. In this embodiment, the reference electrode 36 is maintained at a 250 mv level. By biasing the reference electrode at this level instead of ground, detection of drift by microcomputer 196 is facilitated.

Voltages developed at the indicating electrode 38 are coupled by way of contact pin 74 to an amplifier 212. The amplified signal is converted by converter 206 into digital form for utilization by microcomputer 196. It should be noted that the voltage level at pin 74 encompasses the series circuit comprising the regulated voltage impressed on reference electrode 36, the half cell potential generated at electrode 36, and the half cell potential developed at indicating electrode 38.

Sample detection circuitry 214 is coupled to the output of photocell 82. Detection circuitry 214 operates to provide an output signal over line 209 to microcomputer 196 indicating a change in conduction state of photocell 82. The output of microcomputer 196 is coupled to display 14 and printer 18 in a conventional manner. Display 14 may be a conventional six digit alphanumeric gas discharge display. Printer 18 in this embodiment is a thermoprinter manufactured by Gluton as model No. NP-7.

FIG. 13 shows the details of the components making up the functional blocks shown in FIG. 12. To the extent possible the components making up the functional blocks are encompassed by dotted lines to which common reference numerals have been included to aid the reader in ascertaining the correspondence between the two figures. In view of the detailed nature of FIG. 13, a description of the component by component interconnection will not be necessary to permit one skilled in the art to make and use this invention.

Reference electrode voltage generator 211 is made up of Q4, and AD580JH 2.5 v regulator, and resistor divider R6 and R7. The 2.5 v output is divided down to 0.25 v by the resistors and applied to the reference electrode 36 of the cartridge 22 via pin 76. This 250 mv signal is added to the potential developed by the cartridge electrodes and the sum is applied to the input of the indicating electrode voltage amplifier 212.

The amplifier circuit 212 consists of IC35, a Burr-Brown 3528BM FET input operational amplifier, and its associated components R13, R14, R68 and C27. This circuit gives a non-inverting gain of 20, the gain being established by the ratio of R14 plus trimpot R68 and R13. C27 in combination with R14 gives a $-3$ db roll-off frequency of 4 HZ. This helps filter out noise, particularly 60 HZ. The input resistance of this amplifier, at pin 3, is greater than $10^{12}\Omega$ to keep from loading down the $10^9\Omega$ impedance of the cartridge electrodes. The electrode potential enters the amplifier to coax connector P5. A coax cable 144 connects the amplifier to the cartridge socket assembly 52. The shield of this cable is connected to pin 2 of IC35. Since, through action of the op amp, pin 2 and pin 3 are at the same potential, the shield is at the same potential as the input signal. This reduces leakage currents caused by the length of the coax to zero. The amplifier output, at pin 6, goes to relay K1. A typical electrode potential is 150 mv. This added to the 250 mv reference potential and amplified by 20 gives a typical output voltage of 8 volts.

The cartridge temperature amplifier IC3 is non-inverting with a gain of 6.5. The gain is 1+R58/R57. The input, at pin 3, is the voltage developed across the cartridge temperature thermistor 72. The resistance of the thermistor, and hence this voltage, decreases as temperature increases. The voltage at pin 3 when the thermistor is at 37° is 0.88 v; this times 6.5 gives an output, at pin 6, of 5.72 v. This output goes to relay K1. Trimpot R65 adjusts the op amp input offset voltage to zero.

The voltage-to-frequency converter circuit 206 functions as an A/D converter so that the microcomputer 196 can process analog voltage and temperature information. The input voltage comes in through relay K1. If K1 is deactivated the input is electrode potential (from IC35) and if K1 is activated the input is cartridge temperature (from IC3). K1 is driven by Q6 which is in turn driven by computer-generated signal ETR. ETR, an I/O port in the microcomputer, is set TTL "high" (about 3.5 v) when the computer needs to process temperature information. Conversely, ETR is reset (about 0v) to read electrode voltage.

The converter is an integrating, one-shot (charge pump) type. Its frequency of oscillation is directly proportional to its level of input current. The level of input current is a direct function of input voltage (from K1), being $V_{IN}/(R68+R12)$. So at pin 7 or IC7 there is developed a pulse train whose repetition rate is proportional to the amplitude of the analog input voltage. C20 is the integrating capacitor and C11 is the one-shot capacitor. Resistor network R8–R11, trimpot R64 is used to adjust the input offset voltage of the converter integrator. C25, C26 are supply bypassing capacitors.

The transfer function is made equal to 1KHZ/volt by adjusting slope trimpot R69 and offset trimpot R64. For example, with a typical cartridge electrode generating 150 mv and K1 deactivated, the converter input is 8 v and its output is 8 KHZ. With a cartridge temperature of 37° C. and K1 activated the input is 5.72 v and the output is 5720 HZ.

The pulse waveform at pin 7 of IC7 goes to a flip-flop (not shown) via line 207 and triggers the flip-flop into a change-of-state for every pulse. The microcomputer 196 looks for this change-of-state and increments a register every time it happens. It checks the flip-flop for a period of 1 sec. The count accumulated in the register at the end of 1 sec. is then equal to the number of millivolts of input to the converter. This digital number is processed to carry out the instrument functions.

The sample detector circuit 214 incorporating IC12 and its associated components, uses the changing resistance of a cadmium-sulfide photoresistor 82 to signal microcomputer 196 that a blood-filled capillary tube has been inserted into the cartridge 22. The CdS photocell 82 is in the bottom leg of a resistive voltage divider and thus forms the detector input voltage.

The top leg of this divider is R34. A change in input voltage (at the junction of the cell 82 & R34) causes a voltage to appear at pin 3 of IC12. This voltage is in proportion to the rate-of-change and the amount of change of the input voltage. It is zero if the input is not changing. The differentiator-type response is given by C21 and R33. The voltage on the inverting input (pin 2) of comparator IC12 is formed by divider R32 and trimpot R63. This is adjusted to be about 0.5 v. Since the comparator's non-inverting input (pin 3), the differentiator output, is usually at zero volts, the detector output pin 6 is usually negative and the "sample-in" signal over line 209 that goes to micro-computer 196 is about −0.5 v. CR7, CR8 serve as clamp diodes to make IC12's output TTL compatible.

As noted above, the CdS cell 82 is located in the cartridge socket assembly 52 on one side of the cartridge 22. On the other side, directly opposite, is mounted a green LED 80. The light emitted by the LED 80 shines through the glass electrode channel of the inserted cartridge and then onto the photoresistive cell 82. The light falling on the cell under these conditions causes its resistance to be about 10KΩ; this makes for an input voltage of about 1.4 v to detector circuit 214. Now suppose a blood-filled capillary tube 19 is inserted into the cartridge 22, covering the glass pH electrode 38. The red blood aborbs most of the green light passing through the channel. With only a small amount of light now incident on the cell 82 its resistance increases to about 100KΩ and the detector 214 input voltage increases to about 7.5 v. This change in input voltage of several volts, making the non-inverting comparator IC12 input greater in voltage than the inverting input. The comparator output switches to its positive state and the signal level on line 209 goes to about +5.5 v, signalling microcomputer 196 that a blood sample has been inserted. The comparator IC12 switches back to its negative state when the differentiator voltage decays to 0.5 v, usually within about 1 sec.

Comparator IC11 is the center of the cartridge heater circuit 202. The function of this circuit is to provide power to the cartridge heater elements 66, 68 pressed onto either side of the cartridge 22 when the cartridge is inserted and the door 20 is closed. Heaters 66, 68 are energized until the temperature of the cartridge 22 comes up to approximately 36.5° C. This is required to bring an inserted cartridge up to calibration temperature quickly, about 1 minute. The cartridge temperature sensor thermistor 72 is wired in a voltage divider network. The thermistor 72 makes a press-contact with the cartridge 22 when the door 20 is closed, thereby sensing its temperature. The voltage at point C varies with temperature. The voltage at pin 2 of IC11 is adjusted with trimpot R66 to correspond to a temperature of 36.5° C. which is about 0.899 v. Initially, upon insertion, the cartridge is perhaps 25° C. and the thermistor 72 resistance is high, about 10KΩ, giving a voltage at point C of 1.4 v.

IC11 pin 6 will be positive, turning on Q3 through base resistors R25, 26. When Q3 is on, 32 volts is applied across the heater elements 66, 68, heating the cartridge 22. As the cartridge heats up, the thermistor 72 senses the temperature change, decreasing the voltage at point C. Heat will continue to be applied until the thermistor resistance decreases to about 6.4KΩ, at which point the voltage at point C decreases to just below 0.899 v. The comparator IC11 now switches to its negative voltage state, turning off Q3 and removing power from the heaters 66, 68. When this happens the signal level on line 219 goes from 5.5 v to −0.5 v. The microcomputer 196 senses this and responds by putting a TTL high level on line 210. This turns on Q2 through R23, bringing the base of Q3 to ground. Now Q3 is prevented from turning on; no power can applied to the heaters 66, 68. This is done to insure that cartridge heating cannot upset the measurement of electrode potential during subsequent calibration and pH computation. The heaters stay disabled until a new cartridge is inserted.

R27 and C23 are compensation for IC11. R43 and LED1 give an indication of heater activation. C24 acts as noise filter for the thermistor voltage.

IC13 is configured as an astable multivibrator, providing a ⅔ duty-cycle rectangular waveform, 4 v peak-to-peak, at about 350 HZ on output pin 3. R36, 37 and C22 generates this oscillation condition. C34 provides supply bypassing. The purpose of the oscillator is to disable the cartridge heater elements two-thirds of the time (when the heaters are activated) by turning on Q2 through R35 when pin 3 is high. Turning Q2 on turns Q3 off, removing heater power. The average power of the heaters is reduced thereby resulting in a more desirable rate-of-heating of the cartridge.

Comparator IC6 and its related components make up the forced air heater circuit 198. This circuit is similar to the one just described. A thermistor 178 is mounted on the side of the cartridge socket assembly 52 and senses the temperature of the forced air flowing past it. The air is maintained at 37° C. through action of the comparator. Pin 2 of IC6 is adjusted to 0.880 v with trimpot R67. This is equal to the voltage that appears at pin 3 when the thermistor 178 is at 37° C. If the air temperature goes below 37° C. the thermistor resistance increases, making the pin 3 voltage greater than 0.880 v. This causes IC6 to switch to its positive voltage state, at pin 6, and activate the air heater drive circuit 200 that is located on the power supply circuit board. The activation signal is conveyed to the power supply board via 201. A high signal level on AHS triggers a triac (not shown) that applies line voltage to the resistive heaters 174 in the forced-air-duct. The air is heated as it flows across heater 174. When the air temperature increases just past 37° C. the thermistor 178 resistance decreases to the point where the pin 3 voltage is less than 0.880 v and IC6 switches to its negative voltage state, deactivating the drive circuit 200. The air now starts to cool and the cycle repeats and the temperature is maintained at 37° C.

R17 and D5 form a clamp network to keep the activating signal on line 201 from going any more negative than −0.5 v. Q1, driven by computer-generated signal on line 208 through R22, prevents activation of the drive circuit 200 when it is on. The drive circuit 200 is thus disabled when the microcomputer measures cartridge electrode potential. Transients generated by activation of the drive circuit 200 can interfere with the correct measurement of electrode potential.

A. Operation

In operation, the user turns machine 10 on by way of pressing button 16 on the front panel. Door 20 is tilted outwardly and a fresh cartridge 22 is placed into the socket assembly 52. FIG. 8 represents the state of the cartridge at this time. It should now be apparent that the opposing circuit board subassemblies are biased outwardly when door 20 is open so that sensors do not interfere with cartridge insertion. When door 20 is closed the connector 104 abuts a fixed member 199 in housing 12 such that the spring biased circuit boards are clamped about the cartridge to bring the sensors into contact with appropriate areas on the cartridge.

When door 20 is pivoted to its closed position, crusher 150 breaks ampule 26 to introduce the electrolyte solution into channel 32 to cover both the reference 36 and indicating 38 electrodes as shown in FIG. 9. When the door is closed, the contact switch 168 first closes as it makes contact with the ampule 26 and then opens again as the ampule breaks. Microcomputer 196 looks for this open, closed, open sequence to determine proper ampule breakage and subsequent electrolyte distribution. Upon detecting this sequence, microcomputer 196 causes the system to enter a calibration mode. If the cartridge 22 contains no ampule 26 or one already broken, display 14 will read STAND BY until further action is taken by the operator. If the ample 26 does not break for some reason, STAND BY will be displayed for five seconds and then AMPULE will be displayed to indicate the problem.

If the ampule is properly broken, microcomputer 196 causes the system to enter into a calibration mode. With reference to FIG. 12, microcomputer 196 generates a control signal over line 205 to relay K1 which couples the output of cartridge thermistor 72 to the voltage to frequency converter 206. The heater plates 66, 68 which are in contact with the cartridge are energized until the cartridge is brought to about 36.5° C. The provision of heater plates 66, 68 in addition to the forced air heating system 172 permits the cartridge to be heated to within 0.1° C. of the desired temperature very quickly. Ordinarily, the cartridge will be heated to this precise temperature within about one minute. At that time, the comparator IC11 of the heater control circuit 202 switches thereby generating a signal on line 219 to indicate to microcomputer 196 that the cartridge 22 is at the proper temperature. Once the temperature is reached, the state on line 205 is changed to cause relay K1 to couple the output of the electrode amplifier 212 to the converter 206. The electrode potential is checked at eight second intervals and its value is stored in the RAM memory. This is done about five times. After the fifth time, the temperature is measured again via operation of relay K1. If it is within specified limits, microcomputer 196 enters another eight second loop where it checks electrode potential and stores it, checks the drift rate, and checks the temperature.

When the drift rate is within limits, and the other conditions are met, microcomputer 196 causes the system to enter into a ready mode which is displayed on display 14. This means that the blood filled capillary tube 19 can be inserted into the cartridge. Capillary tube 19 is preferably pre-heparinized with ammonium heparin. Capillary tube is held so that the blood column falls to one end and there are no air bubbles therein. The upper end of the capillary tube is sealed. The open end of the tube 19 is then guided down throat 34 until the tip of electrode 38 is covered by the blood as shown in FIGS. 10 and 11. The electrolyte 27 is thereby displaced from the sensitive tip of the indicating electrode 38. As explained in more detail in the above referenced patent application, electrolyte 27 acts as a bridge between the new half cell potential developed at indicating electrode 38 and the half cell potential developed at reference electrode 36. The electrolyte solution 27 is buffered at about 7.24 pH and contains subsequently the same concentration as ions reactant with reference electrode 36 as the liquid under test. In this embodiment, solution 27 has the same chloride ion concentration as blood to thereby prevent the blood chloride ions from diffusing to the reference electrode which may change the half cell potential established during calibration. Since great care is taken to insure that the temperature of the cartridge 22 is maintained at a precise temperature, the only variable is the new half cell potential developed between the blood and the indicating electrode.

When the capillary tube 19 is inserted, the blood interrupts the light path between LED 80 and photoresistor 82 as noted above. Sample detector circuit 214 senses the differential change in the photoresistor 82 output and thereby supplies a signal over line 209 to microcomputer 196 indicating that the sample is in place. After a ten second waiting period to allow the cartridge potential to stabilize, a new potential is measured and used to calculate the pH value of the sample according to the following formula:

$$pH = s(V - V7) + pHB$$

where, $S$ = electrode slope = $1.887 \times 10^{-2}$ pH/mv = $9.434 \times 10^{-4}$ pH/count;

$V$ = new potential in millivolts = number of converter 206 counts;

$V7$ = calibration potential measured prior to sample insertion; and $pHB$ = pH value of cartridge buffer solution 27 = 7.24 pH As noted above, microcomputer 196 generates a signal over line 208 to temporarily disable the heater control circuitry 198 when the measurement takes place.

After the calculation is completed, the pH value is displayed on display 14. Additionally, the time, date, and pH value are printed on printer 18. The pH value on display 14 remains until the cartridge door is opened and the cartridge removed. When the door is closed again the display 14 will read STAND BY, thereby completing the sequence.

In view of the foregoing, it can now be appreciated that the present invention provides an efficiently designed system which requires only minimal interaction with the user and yet provides extremely accurate results. The design of the cartridge socket assembly and related components cooperate to provide reliable sensing of the cartridge parameters and automatic introduction of the electrolyte solution into the cartridge. Additionally, the system provides a means by which the cartridge and liquids contained therein are maintained at a critical temperature to insure accurate measurements. It is known in the art that the pH value of blood will vary with temperature and that the half cell potentials developed by the electrodes are also subject to variances at different temperatures. The present invention provides a means by which this critical temperature is precisely maintained and is achieved rapidly. It is known that inaccurate measurements will result if the blood has started to clot and thus it is imperative that the measurement be made soon after the sample is taken. Note also that provision is made to insure that electrical noise created by the heater systems do not interfere with the accuracy of the electrode potential measuring process.

It should be reiterated that while the preferred embodiment was described in connection with sensing the pH value of blood, the present invention is broadly directed to measuring a variety of electrochemical characteristics of liquids. Therefore, while this invention has been described in connection with a particular example thereof, other modifications will become apparent to one skilled in the art after a study of the specification, drawings and claims.

We claim:

1. In an apparatus for sensing electrochemical activity of a liquid sample in a receptacle, said apparatus including heater means for heating the liquid to a predetermined temperature, the improvement wherein said heater means comprises:

first means having a relatively low thermal mass in contact with the receptacle for quickly bringing the liquid to said predetermined temperature; and second means for heating the air surrounding the receptacle to said predetermined temperature.

2. The apparatus of claim 1 wherein said receptacle comprises a thin walled cartridge having spaced indicating and reference electrodes bridged by a cavity for holding a sample of the liquid in contact with the indicating electrode.

3. The apparatus of claim 2 which further comprises:

socket means for receiving said cartridge, and wherein said first means includes heater plates on opposing faces of the socket for engaging opposite walls of the cartridge when placed in the socket.

4. The apparatus of claim 3 wherein said socket includes biasing means for urging said heater plates against the walls of the cartridge when placed in the socket.

5. The apparatus of claim 4 which further includes:

a housing with a hinged door, said socket being located in said door with the heater plates being arranged to clamp the walls of the cartridge when the door is pivoted towards said housing to a closed position.

6. The apparatus of claim 1 wherein said second means includes a forced air heater system within the housing for maintaining the air adjacent to said cartridge at said predetermined temperature.

* * * * *